United States Patent
Yoshida et al.

(10) Patent No.: US 10,016,367 B2
(45) Date of Patent: Jul. 10, 2018

(54) CELLULOSE MICROPOWDER

(71) Applicant: ASAHI KASEI KABUSHIKI KAISHA, Tokyo (JP)

(72) Inventors: Naoya Yoshida, Tokyo (JP); Yasuhiko Ono, Tokyo (JP); Kazuhiro Obae, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/329,804

(22) PCT Filed: Aug. 3, 2015

(86) PCT No.: PCT/JP2015/071998
§ 371 (c)(1),
(2) Date: Jan. 27, 2017

(87) PCT Pub. No.: WO2016/024493
PCT Pub. Date: Feb. 18, 2016

(65) Prior Publication Data
US 2017/0258728 A1    Sep. 14, 2017

(30) Foreign Application Priority Data
Aug. 12, 2014 (JP) .................. 2014-164482

(51) Int. Cl.
| C08J 3/12 | (2006.01) |
| A61K 9/20 | (2006.01) |
| A61K 9/00 | (2006.01) |
| A61K 31/7008 | (2006.01) |
| A61K 31/12 | (2006.01) |

(52) U.S. Cl.
CPC ............ *A61K 9/2054* (2013.01); *A61K 9/006* (2013.01); *A61K 9/2013* (2013.01); *A61K 9/2018* (2013.01); *A61K 9/2059* (2013.01); *A61K 9/2095* (2013.01); *A61K 31/12* (2013.01); *A61K 31/7008* (2013.01); *C08J 3/12* (2013.01); *C08J 2301/02* (2013.01)

(58) Field of Classification Search
CPC ........... C08J 3/12; A61K 9/2054; A61K 47/38
See application file for complete search history.

(56) References Cited

U.S. PATENT DOCUMENTS

| 4,159,345 | A | 6/1979 | Takeo et al. |
| 7,939,101 | B2 * | 5/2011 | Obae .................. A61K 9/2054 424/465 |
| 2004/0043964 | A1 | 3/2004 | Gomi et al. |
| 2004/0053887 | A1 | 3/2004 | Obae et al. |
| 2007/0028801 | A1 | 2/2007 | Yamasaki et al. |
| 2007/0190017 | A1 | 8/2007 | Yamasaki et al. |
| 2008/0039621 | A1 | 2/2008 | Maruyama et al. |
| 2009/0022791 | A1 | 1/2009 | Obae et al. |
| 2010/0087552 | A1 | 4/2010 | Shiomi et al. |
| 2011/0062630 | A1 | 3/2011 | Honda et al. |
| 2013/0316176 | A1 | 11/2013 | Maruyama et al. |
| 2014/0356427 | A1 | 12/2014 | Tsue et al. |

FOREIGN PATENT DOCUMENTS

| EP | 1903059 A2 | 3/2008 |
| EP | 2745848 A1 | 6/2014 |
| JP | S40-26274 | 11/1965 |
| JP | S56-2047 B2 | 1/1981 |
| JP | S61-211342 A | 9/1986 |
| JP | S63-267731 A | 11/1988 |
| WO | 02/02643 A1 | 1/2002 |
| WO | 02/36168 A1 | 5/2002 |
| WO | 2002/36168 A1 * | 5/2002 |
| WO | 2004/106416 A1 | 12/2004 |
| WO | 2005/073286 * | 8/2005 |
| WO | 2005/073286 A1 | 8/2005 |
| WO | 2006/115198 * | 11/2006 |
| WO | 2006/115198 A1 | 11/2006 |
| WO | 2008/084854 A1 | 7/2008 |
| WO | 2009/142255 A1 | 11/2009 |

OTHER PUBLICATIONS

Schlieout et al, "Powder and Mechanical Properties of Microcrystalline Cellulose with Different Degrees of Polymerization", AAPS PharmSciTech 2002; 3 (2) article 11 (http://www.aapspharmscitech.org).*
International Search Report issued with respect to Application No. PCT/JP2015/071998, dated Nov. 2, 2015.
International Preliminary Report on Patentability issued with respect to Application No. PCT/JP2015/071998, dated Feb. 14, 2017.
Bowen, P. "Particle Size Distribution Measurement from Millimeters to Nanometers and from Rods to Platelets" Journal of Dispersion Science and Technology, Taylor and Francis Group, vol. 23, No. 5, Jan. 1, 2002, pp. 631-662.
European Search Report in respect to European Application No. 15832338.6, dated Mar. 7, 2018.

* cited by examiner

*Primary Examiner* — Carlos A Azpuru
(74) *Attorney, Agent, or Firm* — Greenblum & Bernstein, P.L.C.

(57) ABSTRACT

The present invention relates to a cellulose powder usable for a satisfactory orally disintegrating tablet having excellent compression moldability and well-balanced tablet moldability and disintegration properties, which can obtain excellent ingestion feel without feeling roughness and dryness in the oral cavity, and more particularly to a cellulose powder with an average polymerization degree of 150 to 450, an average particle diameter of not less than 10 μm but less than 100 μm, and a primary particle ratio of 50% or more.

12 Claims, No Drawings

CELLULOSE MICROPOWDER

TECHNICAL FIELD

The present invention relates to a cellulose powder and a composition containing the cellulose powder and one or more active ingredients. The cellulose powder is used in pharmaceutical, food, and other chemical industrial fields, and is particularly useful as an excipient for a pharmaceutical tablet. Also, a powder and granules prepared using the composition, and a tablet containing the powder and granules are also useful for an orally disintegrating tablet that can be taken without water.

BACKGROUND ART

Conventionally, in pharmaceutical, health food, food and other chemical industrial fields, it is widely known that a cellulose powder is used as an excipient to prepare into a molded body containing an active ingredient, for example, a tablet and the like. Particularly, an orally disintegrating tablet that can be taken without water becomes mainstream in recent tablets, and is a dosage form greatly developed in the pharmaceutical formulation field. Recently, an orally disintegrating tablet is manufactured also by the same preparation method as ordinary tablets that is not a special preparation method, but it is originally based on the technologies established by making full use of the compounding ratio of various kinds of additives and excipients, in order to obtain practical tablet hardness and satisfactory disintegration properties and ingestion feel as an orally disintegrating tablet. The formulation based on such technologies is being important as a high value-added formulation, also in product life cycle management (PLCM) of a product, in addition to improvement in quality of life (QOL) to patients. Furthermore, amid the rapid aging of society, an orally disintegrating tablet that is rapidly disintegrated with saliva or a small amount of water greatly contributes to improvement of adherence and compliance, such as convenience in a medical site and ingestability to patients, as a dosage form easily taken even for a patient with low swallowing ability, such as aged people or little children. However, the history of orally disintegrating tablets is short, and there are also technical problems such as the disintegration time and ingestion feel in the oral cavity, and securing of tablet hardness that does not break or wear during manufacture or distribution. Among them, as to ingestion feel, there are many cases that roughness and dryness of powder in which a patient feels when disintegrating a tablet only with the saliva in the oral cavity remain as sense of incongruity, thus satisfactory ingestion feel is not obtained.

Accordingly, development of a technology for manufacturing an orally disintegrating tablet having proper hardness, rapid disintegration properties, and satisfactory ingestion feel without feeling roughness and dryness is desired, and a more highly complete orally disintegrating tablet is expected.

Patent Document 1 describes a cellulose powder with improved compression moldability and liquid component retentiveness by controlling powder physical properties of cellulose powder in a specific range. By using the cellulose powder, it is possible to prepare tablets with high hardness at a low tableting compression force when tableting, and suppress oozing of liquid component from the tablet surface, and it also contributes to prevent tableting troubles. Particularly, powder physical properties are controlled in specific ranges of an average polymerization degree of 150 to 450, an average particle diameter of 30 to 250 µm, and an apparent specific volume of more than 7 cm$^3$/g, and a retention rate of polyethylene glycol with a molecular weight of 400 of 190% or more. However, it is not mentioned at all for disintegration properties and ingestion feel as an orally disintegrating tablet.

Patent Document 2 describes a cellulose crystallite aggregate with an average level-off polymerization degree of 15 to 375, an apparent specific volume of 1.84 to 8.92 cm$^3$/g (apparent density of 7 to 34 lb/ft$^3$), and a particle size of 300 µm or less.

Patent Document 3 describes a pharmaceutical composition consisting of a cellulose powder with an average polymerization degree of 75 to 375 and an apparent specific volume of 1.6 to 3.1 cc/g, containing 2 to 80% by weight of 200 mesh or more components, medicinal ingredients, and other additives.

Patent Document 4 describes a cellulose powder with an average polymerization degree of 150 to 450, an average L/D of particles of 75 µm or less of 2.0 to 4.5, an average particle diameter of 20 to 250 µm, an apparent specific volume of 4.0 to 7.0 cm$^3$/g, an apparent tapping specific volume of 2.4 to 4.5 cm$^3$/g, and an angle of repose of 550 or less.

The cellulose powders obtained by the methods disclosed in Patent Documents 2 to 4 have low compression moldability, thus have a problem that moldability of tablet is insufficient and practical tablet hardness may not be obtained, and it is not mentioned at all for disintegration properties and ingestion feel as an orally disintegrating tablet.

CITATION LIST

Patent Document

Patent Document 1: WO 2004/106416 A
Patent Document 2: JP S40-26274 B
Patent Document 3: JP 556-2047 B
Patent Document 4: WO 2002/02643 A

SUMMARY OF INVENTION

Technical Problem

The cellulose powder disclosed in Patent Document 1 has a retention rate of polyethylene glycol with a molecular weight of 400 of 190% or more. In general, it is said that an orally disintegrating tablet formulated with 15% or more powdered cellulose does not have good ingestion feel since powdered cellulose having good water absorbency absorbs saliva, and generates dryness of powder in the oral cavity. Also, the size of powder in which roughness of the particles is felt in the oral cavity is said to be 100 µm or more. In Examples of Patent Document 1, a powder with an average particle diameter of 100 µm or more is used, and the cellulose powder ratio of the tablet composition is 10% or more. Considering the above, it is assumed that the cellulose powder described in Patent Document 1 is highly probable to have a problem in ingestion feel when used in an orally disintegrating tablet since water absorbency of saliva is also high, and the saliva in the oral cavity is absorbed into the powder to generate dryness together with roughness.

The cellulose powders disclosed in Patent Documents 2 to 4 have low compression moldability, thus high tableting compression force is required for tableting, and consequently, rapid disintegration properties are not obtained, thus it is very difficult to form an orally disintegrating tablet.

It is necessary to increase the content of microcrystalline cellulose for satisfying both tablet hardness and disintegration rate, while it is necessary to decrease the content of microcrystalline cellulose in order to improve ingestion feel (roughness and dryness), thus it has been difficult to satisfy these three requirements at the same time.

Therefore, with the cellulose powders described in Patent Documents 1 to 4, a tablet satisfying necessary hardness as a tablet, and also having satisfactory disintegration properties and ingestion feel as an orally disintegrating tablet could not be produced.

Thus, an object of the present invention is to provide a satisfactory orally disintegrating tablet having excellent compression moldability and well-balanced tablet moldability and disintegration properties, which can obtain excellent ingestion feel without feeling roughness and dryness in the oral cavity.

Solution to Problem

As a result of intensive studies to solve the aforementioned problems, the present inventors have found that, surprisingly, the absorbing capacity when tableting by spray-drying or pulverizing a cellulose powder with an average polymerization degree of 150 to 450 by a specific method is lower than the case when tableting an ordinary cellulose powder that is not spray-dried or pulverized, and ingestion feel of an orally disintegrating tablet that is a problem of cellulose powder is remarkably improved. As a result of the studies, when the cellulose powder has an average particle diameter of 10 to 100 µm and a primary particle ratio of 50% or more, the above object can be achieved even if the mixing ratio of the cellulose powder in a tablet is high. The present invention has been accomplished thereby.

Specifically, the present invention is as follows.

1. A cellulose powder with an average polymerization degree of 150 to 450, an average particle diameter of not less than 10 µm but less than 100 µm, and a primary particle ratio of 50% or more.

2. The cellulose powder described above, wherein particles of the cellulose powder have a ratio of major axis to minor axis (L/D) of 1.8 to 2.8.

3. The cellulose powder described above, wherein the retention rate of polyethylene glycol with an average molecular weight of 400 is less than 190%, a tablet absorbing capacity at a tablet hardness of 60 N is 170% or less, and a tablet hardness at a tableting compression force of 2.0 kN is 130 N or more.

4. Use of any of the cellulose powders described above as an excipient for an orally disintegrating tablet.

5. A method for producing an orally disintegrating tablet comprising mixing 3 to 99% by mass of any of the cellulose powders described above, and 1 to 97% by mass of one or more kinds of components comprising at least a drug or active ingredient of a drug or active ingredient, an excipient, a binder, a disintegrant and a lubricant, and compression molding.

Advantageous Effects of Invention

The cellulose powder of the present invention has various physical properties of compression moldability and rapid disintegration properties, and can produce a tablet having satisfactory tablet hardness and disintegration properties, without feeling roughness and dryness as an orally disintegrating tablet, even much containing this cellulose powder.

DESCRIPTION OF EMBODIMENTS

Hereinbelow, a best mode for carrying out the present invention (hereinafter, simply referred to as "the present embodiment".) will be explained in detail. The present invention is not limited to the following embodiment, and various modifications and changes can be carried out within the scope of the gist of the invention.

(Cellulose Powder)

The average polymerization degree of the cellulose powder of the present invention is preferably 150 to 450. The average polymerization degree is preferably 150 or more since compression moldability increases, and at an average polymerization degree of 450 or less, hydrolysis of cellulose is sufficient, and the cellulose powder does not contain much amorphous part of cellulose, strongly exhibits fibrous property, is not likely to be elastically recovered, and tends to have excellent moldability.

The cellulose powder of the present invention has an average particle diameter of preferably not less than 10 µm but less than 100 µm, more preferably not less than 10 µm but less than 70 µm, and further preferably not less than 10 µm but less than 50 µm. An average particle diameter of 10 µm or more is preferred since the cellulose particles excessively receive an impact on the particle surface when atomized, and are unlikely to aggregate, thus, when mixing with active ingredients, the active ingredients are uniformly dispersed, thereby reducing variations of the active ingredient content in the obtained tablet. Also, when the average particle diameter is 100 µm or more, roughness of particles is felt in the oral cavity, and thus satisfactory ingestion feel is not obtained.

In the particle configuration of the cellulose powder of the present invention, the primary particle ratio is preferably 50% or more, more preferably 60% or more, and further preferably 70% or more.

The primary particle ratio shows a ratio of the number of primary particles to the total number of particles. Specifically, the primary particle ratio is defined by the measurement method described below.

Primary particles are considered as unit particles judged from apparent geometrical form. Aggregated primary particles are referred to as a secondary particle (aggregate, agglomerate). At a primary particle ratio of less than 50%, the particle shape of secondary particle has an effect, and when disintegrating a tablet in the oral cavity, satisfactory ingestion feel is not obtained due to dry feeling of the cellulose powder. Specifically, a secondary particle has a structure with many voids between primary particles constituting the secondary particle, and water and liquid components are likely to enter into the voids. It is considered that, as a result, saliva is absorbed into the cellulose powder when disintegrating a tablet in the oral cavity, and the oral cavity becomes dry by a lack of saliva, thus ingestion feel is degraded.

The cellulose powder of the present invention has a retention rate of polyethylene glycol with an average molecular weight of 400 of preferably less than 190%, and more preferably 180% or less. When it is less than 190%, the saliva absorbed into the cellulose powder when disintegrating a tablet in the oral cavity is little, thus dryness in the oral cavity and degradation of ingestion feel are suppressed. In the cellulose powder of the present invention, the lower limit of the retention rate of polyethylene glycol with an average molecular weight of 400 is not particularly limited, and is usually preferably 100% or more.

The polyethylene glycol retention rate refers to a value of saturated amount of polyethylene glycol retained in the cellulose powder, represented by % by weight based on the cellulose powder. In addition, the average molecular weight of polyethylene glycol is measured by the method according to the measurement method of the average molecular weight of macrogol 4000 in the 14th Revised Japanese Pharmacopoeia (hereinafter, may be simply abbreviated as JP).

The primary particle ratio and the retention rate of polyethylene glycol with an average molecular weight of 400 are different concepts from each other. Specifically, there exist the cellulose powders with a low primary particle ratio having a high or low retention rate of polyethylene glycol with an average molecular weight of 400. It is considered that the former corresponds to a structure with few voids between primary particles constituting the secondary particle (aggregate), and the latter corresponds to a structure with many voids between primary particles constituting the secondary particle (agglomerate).

As to the cellulose powder of the present invention, the absorbing capacity of a tablet obtained by molding the cellulose powder at a tableting compression force so as to have a tablet hardness of 60 N is preferably 170% or less, more preferably not less than 50% but not more than 170%, and further preferably not less than 50% but not more than 160%. When the absorbing capacity is 170% or less, the saliva absorbed into the cellulose powder when disintegrating a tablet in the oral cavity is little, thus dryness in the oral cavity and degradation of ingestion feel are suppressed, as is described above. At an absorbing capacity of 50% or more, a tablet excellent in water absorbency and disintegration properties suitable as an orally disintegrating tablet can be obtained.

The absorbing capacity of a tablet refers to % by weight of a tablet absorbing a saturated amount of water, based on the dry tablet.

The cellulose powder of the present invention has a tablet hardness at a tableting compression force of 2.0 kN of preferably 130 N or more, more preferably 150 N or more, and further preferably 200 N or more. At a tablet hardness of 130 N or more, there is little possibility that a tablet chips and cracks during transportation and storage to cause a problem on the product quality. Here, the tablet hardness much changes depending on tablet diameter, tablet weight, and compression method, but herein shows a hardness of a tablet obtained by putting 0.5 g of cellulose powder in a mortar, and maintaining it at a tableting compression force of 2 kN for 10 seconds, using a round flat pestle with 1.13 cm in diameter, unless otherwise noted.

(Method for Producing Cellulose Powder)

The method for producing the cellulose powder of the present invention will be described below.

The cellulose powder of the present invention is obtained, for example, by drying a cellulose dispersion obtained by dispersing a natural cellulosic material subjected to hydrolysis treatment in a suitable medium. In this case, a solid component containing the cellulosic material subjected to hydrolysis treatment may be isolated from a hydrolysis solution obtained by the hydrolysis treatment, and a dispersion prepared by separately dispersing the isolated solid component in a suitable medium may be dried. When the hydrolysis solution, as it is, forms a cellulose dispersion, this dispersion can be also directly dried.

The natural cellulosic material can be of plant or animal origin, and is, for example, fibrous materials derived from natural products containing cellulose such as wood, bamboo, cotton, ramie, hoya, bagasse, kenaf or bacterial cellulose, and the natural cellulosic material preferably has cellulose I type crystal structure. The raw material may use one kind of natural cellulosic material from the above-described materials, or may use a mixture of two or more such cellulosic materials. Also, these are preferably used in the form of purified pulps although a method for purifying pulps is not particularly restricted, and any pulp including dissolving pulp, kraft pulp or NBKP pulp may be used.

The hydrolysis method may be acid hydrolysis, alkaline oxidative decomposition, hydrothermal degradation, steam explosion or the like, or a combination of two kinds of such methods.

In the above-described preparation method, the medium used when the solid component containing the cellulosic material subjected to the hydrolysis treatment is then dispersed in a suitable medium is not particularly restricted if it is industrially used, and, for example, water and/or an organic solvent may be used. Examples of the organic solvent include alcohols such as methanol, ethanol, isopropyl alcohol, butyl alcohol, 2-methylbutyl alcohol and benzyl alcohol, hydrocarbons such as pentane, hexane, heptane and cyclohexane, ketones such as acetone and ethyl methyl ketone, and the like. Particularly, organic solvents used in pharmaceutical formulations are preferred, and examples include those classified as solvents in "Iyakuhin Tenkazai Jiten 2007 (Japanese Pharmaceutical Excipients Directory 2007)" (published by Yakuji Nippo Limited). Water and organic solvents may be freely used alone or in a combination of two or more, and the dispersion may be once performed in one kind of medium, and removed from the medium, followed by dispersion in a different medium.

The average particle diameter of cellulose dispersion particles present in the cellulose dispersion obtained as described above is preferably 50 μm or more. When the average particle diameter is 50 μm or more, the cellulose powder of the present invention that has a high apparent specific volume and excellent compression moldability and liquid component retentiveness can be obtained, by drying the cellulose dispersion. Particularly, although a dispersion of cellulose with an average particle diameter of less than 50 μm contains a relatively large amount of cellulose dispersion microparticle component, even if the dispersion much containing the microparticle component is dried, it is difficult to obtain a cellulose powder with high liquid component retentiveness because the microparticle component excessively receives an impact on the particle surface when atomized, and thus has a changed surface structure.

In order to obtain cellulose dispersion particles with an average particle diameter of 50 μm or more from the above-described cellulose dispersion, for example, a cellulose dispersion before drying is subjected to dehydration purification at a time, by absorbing water by decantation using a decanter to control the water content to 40% or more, whereby large particles can be formed. In an alternative method, cellulose dispersion particles with an average particle size of 50 μm or more selected by sieving may be separately dispersed in a suitable medium.

In addition, these methods may be used alone or in combination.

The drying method is not particularly restricted, but may be, for example, freeze-drying, spray drying, drum drying, tray drying, flash drying, or vacuum drying. The drying method may be used alone or in combination of two or more. The spraying method when spray drying may be any spraying method of a disc type, pressure nozzle type, pressure two-fluid nozzle type and pressure four-fluid nozzle type. The spraying method may be used alone or in combination of two or more. Spray drying is preferred from the economic viewpoint.

When the spray drying is performed, a very small amount of water-soluble polymer and a surfactant may be added for the purpose of lowering the surface tension of the dispersion, or a blowing agent or gas may be added to the dispersion for the purpose of promoting vaporization rate of the medium.

The kind of nozzle (nozzle type) or disk (rotary atomizer type) in a spray dryer that sprays a cellulose dispersion includes a pressure two-fluid nozzle, a two-fluid nozzle, a twin jet nozzle, a disk type nozzle and a low cap nozzle, and a pressure two-fluid nozzle and a two-fluid nozzle are preferred for improving the primary particle ratio.

Spray dryer is generally called as a spray dryer, and a drying apparatus that instantaneously dries a cellulose dispersion to obtain particles (manufactured by OHKAWARA KAKOHKI CO., LTD., MATSUBO Corporation, GEA Process Engineering Limited, powdering japan, Inc., Japan Chemical Engineering & Machinery Co., Ltd., fujisaki electric Co. LTD.) is used.

When cellulose particles are strongly aggregated each other, it becomes difficult to achieve a primary particle ratio of 50% or more in the pulverization step described below. The aggregation state of cellulose particles is mostly determined according to the spray drying conditions, thus it is preferred to perform a spray drying step in a condition that cellulose particles are not strongly aggregated each other. Specifically, the concentration of the solid component of cellulose dispersion to be sprayed is preferably 20% or less, more preferably 15% or less, and further preferably 10% or less. When the concentration of the solid component of cellulose dispersion to be sprayed is low, the aggregation force of cellulose particles tends to be low.

The cellulose powder after spray drying preferably has an average particle diameter of 30 to 150 µm. Even in the case where the average particle diameter is larger than 100 µm, the average particle diameter can be adjusted to not less than 10 µm but less than 100 µm, by subjecting the cellulose powder to the pulverization step described below.

(Pulverization Step)

In a case where the primary particle ratio of the cellulose powder after the drying step is less than 50%, or in a case where the average particle diameter is larger than 100 µm, it is preferred to pulverize the cellulose powder after the spray drying step. The pulverization can be performed by pulverizing with a pulverizer such as an ultra-centrifugal pulverizer (ZM-200, manufactured by Retsch GmbH), a jet mill (STJ-200, manufactured by SEISHIN ENTERPRISE Co., Ltd.) and a hammer mill (H-12, manufactured by HOSOKAWA MICRON CORPORATION), a bantam mill (AP-B, manufactured by HOSOKAWA MICRON CORPORATION), a pin mill (160Z, manufactured by POWREX CORPORATION), a feather mill (FM, HOSOKAWA MICRON CORPORATION), a hammer mill (HM-600, Nara Machinery Co., Ltd.), a flash mill (FL-250N, DALTON CORPORATION), a ball mill (Emax, Retsch GmbH), a vibrating ball mill (2C, TRU), or a screen mill that allows passing through a screen (U30, POWREX CORPORATION). Particularly, a jet mill pulverizer (STJ-200, manufactured by SEISHIN ENTERPRISE Co., Ltd.) is preferred since it is an air flow type pulverizer that pulverizes particles while allowing particles to collide with each other by high air pressure, and a secondary particle is easily crushed to form primary particles.

The supply amount of powder and the pulverization pressure are important for pulverization conditions of a jet mill pulverizer, and the supply amount when using a jet mill pulverizer (STJ-200, manufactured by SEISHIN ENTERPRISE Co., Ltd.) is preferably 10 to 20 kg/h and further preferably 15 to 20 kg/h. Also, the pulverization pressure is preferably 0.15 to 0.70 MPa, and further preferably 0.30 to 0.50 MPa. When the supply amount of powder and the pulverization pressure are in the above-mentioned ranges, the powder tends to be easily controlled to an average particle diameter of not less than 10 µm but less than 100 µm, and a primary particle ratio of 50% or more.

Also, the cellulose powder particles prepared by the above method preferably have a ratio of major axis to minor axis (L/D) of 1.8 to 2.8. When the ratio of L/D is in the above-mentioned range, ingestion feel is improved, and the kind of medicines usable as an orally disintegrating tablet is increased.

Major axis (L) and minor axis (D) can be measured by a microscope. One hundred particles are observed, the major axis and minor axis of each particle are measured, and the ratio of L/D is calculated, then the average of 100 particles is an L/D of the cellulose powder. The major axis refers to a longest longitudinal-direction length of the particle observed with a microscope, and the minor axis refers to a length of the longest part in a perpendicular direction to the major axis. When the pulverization conditions are too strong, primary particles are excessively crushed, and L/D tends to be small. Also, when the pulverization conditions are too weak, long narrow particles are not pulverized, and L/D tends to be large. In order to have L/D in the range of 1.8 to 2.8, it is necessary to appropriately set the pulverization conditions. With the supply amount of powder and the pulverization pressure described above, L/D tends to be mostly adjusted in the range of 1.8 to 2.8. Even if L/D is out of the range of 1.8 to 2.8, L/D can be controlled to an appropriate range by properly adjusting the supply amount of powder and the pulverization pressure.

(Orally Disintegrating Tablet)

The orally disintegrating tablet referred in the present invention contains one or more kinds of drugs or effective ingredients (hereinafter, also referred to as "active ingredients") and the cellulose powder of the present invention. A method for producing the orally disintegrating tablet can be carried out by a known method of mixing of each component, stirring, granulating, sizing, and tableting, etc.

In the orally disintegrating tablet of the present invention, the addition rate of the cellulose powder of the present invention described above is preferably 3% by mass or more, more preferably 10% by mass or more, and further preferably 15% by mass or more. The addition rate is preferably 3% by mass or more, since moldability of tablet is improved and practical tablet hardness is obtained. In the orally disintegrating tablet of the present invention, the addition rate of the cellulose powder of the present invention is preferably 99% by mass or less.

The active ingredient in the orally disintegrating tablet of the present invention includes pharmaceutical medicinal ingredients, health food components, and food components. It is also possible to use the cellulose powder of the present invention by mixing with a cosmetic component, a pigment, a flavor, a catalyst, and a surfactant. The form of active ingredients may be in any form of powder, crystal, oil, liquid or semisolid. Also, they may be subjected to coating for the purpose of controlling elution, reducing bitterness, and the like. The active ingredient may be used alone or in combination of two or more.

For example, pharmaceutical medicinal ingredients among active ingredients include orally administered ingredients such as antiepileptic agents, antipyretic-analgesic-antiinflammatory agents, neuropsychiatric agents, skeletal muscle relaxants, hypnosedative agents, antihypnotic agents, antivertigo agents, infant analgesic agents, stomachic agents, antacid agents, digestive agents, cardiotonic agents, antiarrhythmic agents, antihypertensive agents, vasodilative agents, diuretic agents, antiulcer agents, antiflatulent agents, therapeutic agents for osteoporosis, antitussive expectorant agents, antiasthmatic agents, antifungus agents, micturition improvement agents, revitalizer, and vitamin agents. Medicinal ingredients may be freely used alone or in combination of two or more. Specific examples include antiepileptic agents (phenytoin, acetylpheneturide, trimethadione, phenobarbital, primidone, nitrazepam, sodium valproate, sultiame, and the like), antipyretic-analgesic-antiinflammatory agents (acetaminophen, phenylacetylglycine methyl amide, mefenamic acid, diclofenac sodium, floctafenine, aspirin, aspirin aluminum, ethenzamide, oxyphenbutazone, sulpyrine, phenylbutazone, ibuprofen, alclofenac, naloxene, ketoprofen, tinoridine hydrochloride, benzydamine hydrochloride, tiaramide hydrochloride, indomethacin, piroxicam, salicylamide, and the like), antivertigo agents (dimenhydrinate, meclizine hydrochloride, difenidol hydrochloride, and the like), narcotics (opium alkaloid hydrochloride, morphine hydrochloride, codeine phosphate, dihydrocodeine phosphate, oxymetebanol, and the like), neuropsychiatric agents (chlorpromazine hydrochloride, levomepromazine maleate, perazine maleate, propericiazine, perphenazine, chlorprothixene, haloperidol, diazepam, oxazepam, oxazolam, mexazolam, alprazolam, zotepine, and the like), skeletal muscle relaxants (chlorzoxazone, chlorphenesin carbamate, chlormezanone, pridinol mesylate, eperisone hydrochloride, and the like), autonomic nerve agents (bethanechol chloride, neostigmine bromide, pyridostigmine bromide, and the like), anti-spasmodic agents (atropine sulfate, butropium bromide, butylscopolamine bromide, propantheline bromide, papaverine hydrochloride, and the like), antiparkinsonian agents (biperiden hydrochloride, trihexyphenidyl hydrochloride, amantadine hydrochloride, levodopa, and the like), antihistaminic agents (diphenhydramine hydrochloride, dl-chlorpheniramine maleate, promethazine, mequitazine, clemastine fumarate, and the like), cardiotonic agents (aminophylline, caffeine, dl-isoproterenol hydrochloride, etilefrine hydrochloride, norfenerine hydrochloride, ubidecarenone, and the like), antiarrhythmic agents (procainamide hydrochloride, pindolol, metoprolol tartrate, disopyramide, and the like), diuretic agents (potassium chloride, cyclopenthiazide, hydrochlorothiazide, triamterene, acetazolamide, furosemide, and the like), hypotensive agents (hexamethonium bromide, hydralazine hydrochloride, syrosingopine, reserpine, propranolol hydrochloride, captopril, methyldopa, and the like), vasoconstrictor agents (dihydroergotamine mesylate and the like), vasodilator agents (etafenone hydrochloride, diltiazem hydrochloride, carbocromen hydrochloride, pentaerythritol tetranitrate, dipyridamole, isosorbide nitrate, nifedipine, nicametate citrate, cyclandelate, cinnarizine, and the like), antiarteriosclerotic agents (ethyl linoleate, lecithin, clofibrate, and the like), cardiovascular agents (nicardipine hydrochloride, meclofenoxate hydrochloride, cytochrome C, pyridinolcarbamate, vinpocetine, calcium hopantenate, pentoxifylline, idebenone, and the like), respiratory stimulants (dimefline hydrochloride and the like), antitussive expectorant agents (codeine phosphate, dihydrocodeine phosphate, dextromethorphan hydrobromide, noscapine, L-methylcysteine hydrochloride, bromhexine hydrochloride, theophylline, ephedrine hydrochloride, amlexanox, and the like), cholagogues (osalmid, phenylpropanol, hymecromone, and the like), intestinal regulators (berberine chloride, loperamide hydrochloride, and the like), agents for digestive organs (metoclopramide, fenipentol, domperidone, and the like), vitamin agents (retinol acetate, dihydrotachysterol, etretinate, thiamine hydrochloride, thiamine nitrate, fursultiamine, octotiamine, cycotiamine, riboflavin, pyridoxine hydrochloride, pyridoxal phosphate, nicotinic acid, pantethine, cyanocobalamin, biotin, ascorbic acid, phytonadione, menatetrenone, and the like), antibiotics (benzathine benzylpenicillin, amoxicillin, ampicillin, cyclacillin, cefaclor, cephalexin, cefuroxime axetil, erythromycin, kitasamycin, josamycin, chloramphenicol, tetracycline, griseofulvin, cefuzonam sodium, and the like), and chemotherapeutic agents (sulfamethoxazole, isoniazid, ethionamide, thiazosulfone, nitrofurantoin, enoxacin, ofloxacin, norfloxacin, and the like).

The other active ingredients include caffeine, lansoprazole, famotidine, omeprazole, mosapride citrate, voglibose, zolpidem tartrate, loratadine, imidapril hydrochloride, mizoribine, cefcapene pivoxil hydrochloride, levofloxacin, risperidone, sumatriptan succinate, quetiapine fumarate, solifenacin succinate, glucosamine, glucosamine hydrochloride, N-acetyl glucosamine, coenzyme Q10, Gymnema, *Agaricus*, collagen, psyllium husk powder, chondroitin, chondroitin sulfate, turmeric, alginic acid, sodium alginate, alginic acid esters, zinc alginate, potassium alginate, calcium alginate, ammonium alginate, Bofutsushosan, *Angelica keiskei*, astaxanthin, alpha lipoic acid, ginkgo leaf, elastin, L-carnitine, chitosan, chlorella, spirulina, ceramide, saw palmetto, hyaluronic acid, bilberry, β-glucan, Maca, pine bark extract, lutein, African mango eaves, citrus fruit extract, mushroom chitosan, Kudzu flower extract, green coffee bean extract, green rooibos, black vinegar, ornithine, amino acid, olive, curcumin, *Agaricus*, fungi such as *Ganoderma lucidum*, phospholipids, oligo-lactic acid, ferulic acid, green soybean powder, lactobionic acid, cat's claw, polyphenols, and the like.

Examples of other oily and liquid active ingredients include pharmaceutical medicinal ingredients described in "the 16th Revised Japanese Pharmacopoeia" (published by Hirokawa-Shoten Ltd.), "JPC", "USP26", "NF21" (all published by the UNITED STATES PHARMACOPEIAL CONVENTION, INC), and "EP", and the like, such as teprenone, indomethacin farnesyl, dimethicone, menatetrenone, phytonadione, vitamin A oil, fenipentol, vitamins such as vitamin D and vitamin E, DHA (docosahexaenoic acid), EPA (eicosapentaenoic acid), higher unsaturated fatty acids such as liver oil, coenzyme Qs, oil-soluble flavors such as orange oil, lemon oil and peppermint oil. For vitamin E, there are various homologues and derivatives thereof, and it is not particularly limited as long as they are in liquid form at ordinary temperature. Examples thereof include dl-α-tocopherol, dl-α-tocopherol acetate, d-α-tocopherol, d-α-tocopherol acetate, and the like. The ingredients selected from the above may be freely used alone or in combination of two or more.

Examples of semisolid active ingredients include Chinese herbal medicines or crude drug extracts such as earthworm, licorice, cassia bark, peony root, moutan bark, Japanese valerian, zanthoxylum fruit, ginger, citrus unshiu peel, ephedra herb, nandina fruit, yellow bark, polygala root, platycodon root, plantago seed, plantago herb, shorttube lycoris, senega root, fritillaria bulb, fennel, phellodendron bark, coptis rhizome, zedoary, matricaria, gentian, oriental bezoar, animal bile, adenophorae radix, ginger, atractylodes lancea rhizome, clove, citrus unshiu peel, atractylodes rhizome, panax rhizome, ginseng, kakkonto, keihito, kousosan, saikokeishito, shosaikoto, shoseiryuto, bakumondoto, hangekobokuto, and maoto, an oyster meat essence, propolis and an extract thereof, coenzyme Qs, and the like. The ingredients selected from the above may be freely used alone or in combination of two or more.

In addition to the active ingredients and the cellulose powder, the orally disintegrating tablet of the present invention may also contain other components such as a disintegrant, a binder, a fluidizing agent, an excipient, a lubricant, a flavoring agent, a perfume, a coloring agent, a sweetening agent, and a high sweetening agent, as necessary. These components are preferably 1 to 97% by mass, and more preferably 1 to 90% by mass, in total with the active ingredients. Also, in the orally disintegrating tablet of the present invention, the addition rate of one or more kinds of components comprising at least an active ingredient among a drug or effective ingredient (active ingredient), an excipient, a binder, a disintegrant and a lubricant is preferably 1 to 97% by mass.

Disintegrants include components usable for formulations and foods, such as those classified as disintegrant in "Iyakuhin Tenkabutsu Jiten 2000 (Japanese Pharmaceutical Excipients Directory 2000)" (published by Yakuji Nippo Limited) such as celluloses such as croscarmellose sodium, carmellose, carmellose calcium, carmellose sodium and hydroxypropyl cellulose of low degree of substitution, starches such as sodium carboxymethyl starch, hydroxypropyl starch, rice starch, wheat starch, corn starch, potato starch and a partially pregelatinized starch, and synthetic polymers such as crospovidone and crospovidone copolymer, and other additives. The disintegrants selected from the above may be freely used alone or in combination of two or more.

Binders and saccharides include those classified as binder in "Iyakuhin Tenkabutsu Jiten 2007 (Japanese Pharmaceutical Excipients Directory 2007)" (published by Yakuji Nippo Limited) such as saccharides such as sucrose, glucose, lactose and fructose, sugar alcohols such as mannitol, xylitol, maltitol, erythritol and sorbitol, water-soluble polysaccharides such as gelatin, pullulan, carrageenan, Locust bean gum, agar, glucomannan, xanthan gum, tamarind gum, pectin, sodiumalginate and gum arabic, celluloses such as microcrystalline cellulose, powdered cellulose, hydroxypropyl cellulose and methylcellulose, starches such as a pregelatinized starch and starch glue, synthetic polymers such as polyvinylpyrrolidone, carboxy vinyl polymer and polyvinyl alcohol, and inorganic compounds such as calcium hydrogenphosphate, calcium carbonate, synthetic hydrotalcite and magnesium aluminosilicate. Those selected from the above may be freely used alone or in combination of two or more.

Fluidizing agents include those classified as fluidizing agent in "Iyakuhin Tenkabutsu Jiten 2007 (Japanese Pharmaceutical Excipients Directory 2007)" (published by Yakuji Nippo Limited) such as silicon compounds such as hydrous silicon dioxide and light anhydrous silicic acid. The fluidizing agents selected from the above may be freely used alone or in combination of two or more.

Lubricants include those classified as lubricant in "Iyakuhin Tenkabutsu Jiten 2007 (Japanese Pharmaceutical Excipients Directory 2007)" (published by Yakuji Nippo Limited) such as magnesium stearate, calcium stearate, stearic acid, sucrose fatty acid ester and talc. The lubricants selected from the above may be freely used alone or in combination of two or more.

Flavoring agents include those classified as flavoring agent in "Iyakuhin Tenkabutsu Jiten 2007 (Japanese Pharmaceutical Excipients Directory 2007)" (published by Yakuji Nippo Limited) such as glutamic acid, fumaric acid, succinic acid, citric acid, sodium citrate, tartaric acid, malic acid, ascorbic acid, sodium chloride and 1-menthol. The flavoring agents selected from the above may be freely used alone or in combination of two or more.

Perfumes include those classified as aromatizing agent or perfume in "Iyakuhin Tenkabutsu Jiten 2007 (Japanese Pharmaceutical Excipients Directory 2007)" (published by Yakuji Nippo Limited) such as oils such as orange, vanilla, strawberry, yoghurt, menthol, fennel oil, cinnamon oil, orange peel oil and peppermint oil, and green tea powder. The perfumes selected from the above may be freely used alone or in combination of two or more.

Coloring agents include those classified as coloring agent in "Iyakuhin Tenkabutsu Jiten 2007 (Japanese Pharmaceutical Excipients Directory 2007)" (published by Yakuji Nippo Limited) such as food dyes such as Food Red No. 3, Food Yellow No. 5 and Food Blue No. 1, sodium copper chlorophyllin, titanium oxide, and riboflavin. The coloring agents selected from the above may be freely used alone or in combination of two or more.

Sweetening agents and high sweetening agents include those classified as sweetening agent in "Iyakuhin Tenkabutsu Jiten 2007 (Japanese Pharmaceutical Excipients Directory 2007)" (published by Yakuji Nippo Limited) such as aspartame, saccharin, glycyrrhizic acid dipotassium salt, stevia, maltose, maltitol, sucralose, fructose, xylitol, starch syrup and powdered sweet hydrangea leaf. The sweetening agents selected from the above may be freely used alone or in combination of two or more.

(Method for Producing Orally Disintegrating Tablet)

The orally disintegrating tablet of the present invention refers to a composition comprising the cellulose powder of the present invention and one or more active ingredients, and other additives as necessary, wherein the composition is a tablet obtained by compression molding. As the method for producing an orally disintegrating tablet of the present invention, a method comprising mixing the cellulose powder of the present invention, one or more active ingredients, and other additives as necessary, and compression molding the obtained mixture is preferred, and more specifically, a method comprising mixing 3 to 99% by mass of the cellulose powder of the present invention, and 1 to 97% by mass of one or more kinds of components comprising at least a drug or active ingredient of a drug or active ingredient, an excipient, a binder, a disintegrant and a lubricant, and compression molding the obtained mixture is more preferred.

A tablet formulated with the cellulose powder of the present invention can obtain practical hardness by a simple and easy method such as direct tableting without going through a complex process. However, any production method including a dry granule compression method, a wet granule compression method, a compression method with extragranular addition of an excipient or a method for preparing a multicore tablet using, as inner core, a tablet preliminarily subjected to compression molding may be also used.

Methods for producing a tablet composition that comprises one or more active ingredients and the cellulose powder of the present invention as main components will be described below. However, the production method of the present invention is not limited to the following methods. The active ingredient referred herein may have any form of solid, liquid, and semisolid, and the active ingredient may be used alone, or used by the dissolution, suspension, or emulsification thereof in a medium.

Examples of the production methods include the following methods:

i) a production method which comprises mixing the cellulose powder of the present invention with a single active ingredient, and compression molding the mixture;

ii) a production method which comprises mixing an active ingredient preliminarily dissolved or dispersed in water with the cellulose powder of the present invention, and compression molding the mixture;

iii) a production method which comprises preliminarily dissolving an active ingredient in a small amount of an organic solvent, dispersing it in water, mixing this dispersion with the cellulose powder of the present invention, and compression molding the mixture;

iv) a production method which comprises mixing an active ingredient preliminarily dissolved or dispersed in a water-soluble polymer or a water-soluble polymer aqueous solution with the cellulose powder of the present invention, and compression molding the mixture; and v) a production method which comprises mixing an active ingredient preliminarily dissolved or dispersed in oil and fat with the cellulose powder of the present invention, and compression molding the mixture.

In addition, an active ingredient preliminarily dissolved in a large amount of an organic solvent may be mixed with the cellulose powder of the present invention, followed by compression molding the mixture using a well-known method. However, the use of this production method requires the drying of the obtained tablet to remove the organic solvent.

Of the above-described production methods, in the case of i) production method which comprises mixing the cellulose powder of the present invention with a single active ingredient, and compression molding the mixture, other components including, so-called, solubilizing agent such as surfactant or oil and fat, a disintegrant, a binder, a fluidizing agent, a lubricant, a flavoring agent, a perfume, a coloring agent or a sweetening agent may be added as necessary when mixing, in addition to the cellulose powder of the present invention and the active ingredient. The other components may be used alone or in a combination of two or more. The order of addition and mixing of these components is not restricted, and the active ingredient may be added to and mixed with the cellulose powder of the present invention, the cellulose powder of the present invention may be added to and mixed with the active ingredient, or both may be collectively added and mixed. When other components are added in addition to the cellulose powder of the present invention and an active ingredient, the cellulose powder of the present invention may be added to and mixed with other components which are preliminarily mixed with the active ingredient, the active ingredient may be added to and mixed with other components which are preliminarily mixed with the cellulose powder of the present invention, other components may be added to and mixed with the cellulose powder of the present invention which is preliminarily mixed with the active ingredient, or all of the components may be collectively added and mixed.

A method for adding the active ingredient is not particularly restricted as long as it is a method usually carried out, and the addition may be continuously or collectively performed using a small-size sucking transporter, an air transporter, a bucket conveyor, a force-feed type conveying device, a vacuum conveyor, an oscillating type constant quantity feeder, a spray, a funnel or the like.

A mixing method is not particularly restricted as long as it is a method usually carried out, and it may use a vessel rotation type mixer such as a V type, W type, double corn type or container tack type mixer, a stirring mixer such as a high-speed agitation type, universal agitation type, ribbon type, pug type or nautor type mixer, a high speed fluid type mixer, a drum type mixer, or a fluidized bed type mixer. In addition, a vessel shaking type mixer such as a shaker can be also used.

A method for the compression molding of the composition is not particularly restricted as long as it is a method usually carried out, and a method of compression molding the composition into a desired form using a mortar and a pestle or a method of preliminarily compression molding the composition into a sheet form and then cutting it into a desired form may be used. A compression molding machine can use, for example, a roller type press such as a hydrostatic press, a briquetting roller type press or a smoothing roller type press, or a compressor such as a single-punch tableting machine or a rotary tableting machine.

Of the above-described production methods, in the case of ii) production method which comprises mixing an active ingredient preliminarily dissolved or dispersed in water with the cellulose powder of the present invention and compression molding the mixture, so-called, solubilizing agent such as surfactant or oil and fat, and the like may be added as necessary in dissolving or dispersing the active ingredient in water as pretreatment. These may be used alone or in a combination of two or more. The order of the addition and mixing of these components in dissolution or dispersion is not particularly restricted, and the active ingredient may be added to and mixed with water, water may be added to and mixed with the active ingredient, or both may be collectively added and mixed. When a solubilizing agent is added, a mixture of the active ingredient and the solubilizing agent may be added to and mixed with water, the active ingredient may be added to and mixed with the solubilizing agent dissolved or dispersed in water, or all of the components may be collectively added and mixed.

A dissolution or dispersion method is not particularly restricted as long as it is a dissolution or dispersion method usually carried out, and a stirring/mixing method such as a portable mixer, a spatial mixer, a side mixer or the like using the stirring blade of the one-way rotating, multi-shaft rotary, reciprocating/reversing, vertically moving, rotating+vertically moving or duct type, a jet-type stirring/mixing method such as a line mixer, a gas-blowing stirring/mixing method, a mixing method using a high-shear homogenizer, a high-pressure homogenizer, an ultrasonic homogenizer or the like, or a vessel shaking type mixing method using a shaker or the like may be used.

When the solution or dispersion obtained by the above-described method and the cellulose powder of the present invention are mixed, other components such as a disintegrant, a binder, a fluidizing agent, a lubricant, a flavoring agent, a perfume, a coloring agent, a sweetening agent or a solubilizing agent may be added. These may be used alone or in a combination of two or more. The order of addition and mixing of these components is not restricted, and the active ingredient solution or dispersion may be added to and mixed with the cellulose powder of the present invention, the cellulose powder of the present invention may be added to and mixed with the active ingredient solution or dispersion. Also, when other components are added in addition to the cellulose powder of the present invention and the active ingredient solution or dispersion, the active ingredient solution or dispersion may be added to and mixed with other components which are preliminarily mixed with the cellulose powder of the present invention, the cellulose powder of the present invention may be added to and mixed with other components which are preliminarily mixed with the active ingredient solution or dispersion, other components may be added to and mixed with the cellulose powder of the present invention which is preliminarily mixed with the active ingredient solution or dispersion, or all of each the components may be collectively added and mixed.

In these cases, the adding, mixing, and compression molding methods are not particularly restricted as long as they are methods usually carried out, and the methods illustrated as an example in the production method i) may be also used.

As the production method, in the case of iii) production method which comprises preliminarily dissolving an active ingredient in a small amount of an organic solvent and then dispersing it in water, mixing this dispersion with the cellulose powder of the present invention and compression molding the mixture, the dissolution of the active ingredient in a small amount of an organic solvent as pretreatment does not particularly restrict the order of addition, and the active ingredient may be added to and mixed with the organic solvent, the organic solvent may be added to and mixed with the active ingredient, or both may be collectively added and mixed. In dispersing the active ingredient solution in water, one or more solubilizing agents may be used in combination therewith. In these cases, the order of addition is not particularly restricted, and a mixture of the active ingredient solution and the solubilizing agent may be added to and mixed with water, the active ingredient solution may be added to and mixed with the solubilizing agent dissolved or dispersed in water, the solubilizing agent may be added to and mixed with a mixture of water and the active ingredient solution, or all of the components may be collectively added and mixed.

The dissolving or dispersing method is not particularly restricted as long as it is a dissolving or dispersing method usually carried out, and the dissolving or dispersing method illustrated as an example in the production method (ii) may be used. When the active ingredient solution or dispersion obtained by the above-described method and the cellulose powder of the present invention are mixed, a disintegrant, a binder, a fluidizing agent, a lubricant, a flavoring agent, a perfume, a coloring agent, a sweetening agent, a solubilizing agent and the like may be added as necessary. These may be used alone or in a combination of two or more. In these cases, the adding, mixing and compression molding methods are not particularly restricted, and the methods illustrated as an example in the production method i) may be used.

As the production method, in the case of iv) production method which comprises mixing an active ingredient preliminarily dissolved or dispersed in a water-soluble polymer or a water-soluble polymer aqueous solution with the cellulose powder of the present invention and compression molding the mixture, a solubilizing agent may be added as necessary in dissolving or dispersing the active ingredient in the water-soluble polymer or the water-soluble polymer aqueous solution as pretreatment. The order of addition of these components is not particularly restricted, and for example, the active ingredient may be added to and mixed with the water-soluble polymer or water-soluble polymer aqueous solution, the water-soluble polymer or water-soluble polymer aqueous solution may be added to and mixed with the active ingredient, or both may be collectively added and mixed. When a solubilizing agent is added, the order of addition is not also particularly restricted, and a mixture of the active ingredient and the solubilizing agent may be added to and mixed with the water-soluble polymer or water-soluble polymer aqueous solution, a mixture of the water-soluble polymer or water-soluble polymer aqueous solution and the solubilizing agent may be added to and mixed with the active ingredient, a mixture of the active ingredient and the water-soluble polymer or water-soluble polymer aqueous solution may be added to and mixed with the solubilizing agent, or all of the components may be collectively added and mixed.

When the active ingredient solution or dispersion obtained by the above-described method and the cellulose powder of the present invention are mixed, a disintegrant, a binder, a fluidizing agent, a lubricant, a flavoring agent, a perfume, a coloring agent, a sweetening agent, a solubilizing agent and the like may be added as necessary. These may be used alone or in a combination of two or more. In these cases, the adding, mixing and compression molding methods are not particularly restricted, and the methods illustrated as an example in the production method i) may be used.

As the production method, in the case of v) production method which comprises mixing an active ingredient preliminarily dissolved or dispersed in fat and oil with the cellulose powder of the present invention and compression molding the mixture, a solubilizing agent may be added in dissolving or dispersing the active ingredient in oil and fat as pretreatment. The adding, dissolution or dispersion method of these components is not particularly restricted, and the methods illustrated as an example in the production method i) may be used. When the obtained solution or dispersion and the cellulose powder of the present invention are mixed, a disintegrant, a binder, a fluidizing agent, a lubricant, a flavoring agent, a perfume, a coloring agent, a sweetening agent, a solubilizing agent and the like may be added as necessary. These may be used alone or in a combination of two or more. In these cases, the adding, mixing and compression molding methods are not particularly restricted, and the methods illustrated as an example in the production method i) may be used.

In these production methods, particularly when the active ingredient is poorly soluble in water, the resulting composition can have the solubility or dispersibility of the active ingredient in water improved by using production methods i) to v) involving the addition of a solubilizing agent or production methods iii), iv), and v) that do not involve the addition of the solubilizing agent. Also, when various polyethylene glycols are used as a solubilizing agent at this time, these also act as protection components of the drug, thus decomposition of the drug in a body is suppressed, and sustainability of drug action can be improved.

Organic solvents used in the above-described production method are not particularly restricted if they are used in pharmaceuticals, and examples thereof include those classified as solvent in "Iyakuhin Tenkazai Jiten 2007 (Japanese Pharmaceutical Excipients Directory 2007)" (published by Yakuji Nippo Limited) such as alcohols such as methanol and ethanol and ketones such as acetone, and these may be freely used alone or in a combination of two or more.

Examples of water-soluble polymers include water-soluble polymers described in "Iyakuhin Tenkazai Jiten 2007 (Japanese Pharmaceutical Excipients Directory 2007)"

(published by Yakuji Nippo Limited) such as hydroxypropyl cellulose, hydroxypropyl methylcellulose, polyacrylic acid, carboxy vinyl polymer, polyethylene glycol, polyvinyl alcohol, polyvinylpyrrolidone, methylcellulose, ethylcellulose, gum arabic and starch glue, and these may be freely used alone or in a combination of two or more.

Examples of oil and fats include oil and fats described in "Iyakuhin Tenkazai Jiten 2007 (Japanese Pharmaceutical Excipients Directory 2007)" (published by Yakuji Nippo Limited) such as stearic acids such as monoglyceride stearate, triglyceride stearate and sucrose stearate, paraffins such as liquid paraffin, carnauba wax, hydrogenated oils such as hydrogenated castor oil, castor oil, stearic acid, stearyl alcohol and polyethyleneglycol, and these may be freely used alone or in a combination of two or more.

Examples of surfactants include those classified as a surfactant in "Iyakuhin Tenkazai Jiten 2007 (Japanese Pharmaceutical Excipients Directory 2007)" (published by Yakuji Nippo Limited) such as phospholipid, glycerin fatty acid ester, polyethylene glycol fatty acid ester, sorbitan fatty acid ester, polyoxyethylene hydrogenated castor oil, polyoxyethylene cetyl ether, polyoxyethylene stearyl ether, polyoxyethylene nonylphenyl ether, polyoxyethylene polyoxypropylene glycol, polyoxyethylene sorbitan monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate and sodium lauryl sulfate, and these may be freely used alone or in a combination of two or more. In addition to using the form of a tablet obtained by compression molding as described above, the composition for a tablet of the present invention may be used in the form of a granule or a powder particularly for the purpose of improving flowability, blocking resistance and aggregation resistance because the composition is excellent in liquid component retentiveness.

Specific methods for tableting the orally disintegrating tablet of the present invention will be described.

Examples thereof include a method of preparing a powder for tableting by mixing an active ingredient and a cellulose powder, and an additive comprising a saccharide, a sugar alcohol or the like with a suitable mixer, and then tableting the obtained powder. Tableting can be produced, for example, by a known tableting device such as a rotary tableting machine or a single-punch tableting machine. The compression force at tableting is desirably as low as possible and is preferably 20 kN or less, more preferably 15 kN or less, and further preferably 10 kN or less. The tableting compression force and disintegration properties of tablet have a correlation with the porosity in the tablet and water permeation, thus the tableting compression force is preferably low, also for securing disintegration properties as an orally disintegrating tablet.

The orally disintegrating tablet has a tablet hardness of preferably not less than 50 N but less than 200 N, more preferably not less than 50 N but less than 150 N, and further preferably not less than 50 N but less than 100 N. A tablet hardness of 50 N or more is preferred since the side surface of a tablet is unlikely to chip and crack during transportation and storage. On the other hand, disintegration properties of tablet do not get late at a tablet hardness of less than 200 N, and disintegration properties satisfactory as an orally disintegrating tablet are obtained.

The orally disintegrating tablet is a pharmaceutical, a health food formulation or the like that can be taken without water, and for example, the disintegration time of a tablet carried out according to the 16th Revised Japanese Pharmacopoeia, General Tests, Processes and Apparatus "Disintegration Test", is preferably less than 60 seconds and more preferably 30 seconds or less.

Also, in an oral disintegration test that actually puts a tablet into someone's mouth to allow the tablet to be disintegrated only with the saliva, it is preferred to be disintegrated in less than 60 seconds and more preferably 30 seconds or less.

EXAMPLES

The present invention will be described with reference to Examples and Comparative Examples. However, the present invention is not limited thereto.

Methods and conditions for measuring physical properties used in the present invention are as follows.

<Average Polymerization Degree>

The degree used a value determined by the copper ethylenediamine solution viscosity method described in the Identification Test for Microcrystalline Cellulose (3) of the 16th Revised Japanese Pharmacopoeia.

<Average Particle Diameter [µm] of Particles>

The particle diameter was measured using a laser diffraction/scattering particle size distribution meter (LA-910, manufactured by Horiba, Ltd.). The average particle diameter was calculated as the number average of volume frequencies.

<Apparent Bulk Density [g/Ml]>

The volume of a particle layer obtained by loosely filling 30 g of particles in a 100 ml cylinder was read, and the value was calculated by dividing the read value by 30. The number of repetitions was 3, and the average thereof was obtained.

<Retention Rate of Polyethylene Glycol (PEG) with Average Molecular Weight of 400 [% by Weight]>

2.0 g of a cellulose powder was kneaded on a glass board using a spatula each time while adding dropwise polyethylene glycol (macrogol 400, manufactured by Sanyo Chemical Industries, Ltd.) from a burette to use, as an end point, the point at which macrogol bleeds out on the powder surface, and the saturated retention rate was calculated by the formula of "Weight of polyethylene glycol g×100/Weight of cellulose powder (2.0 g)".

<Primary Particle Ratio>

Using a dry image analyzer (Malvern, Morphorogi G3S), about 10,000 particles were photographed, and image analysis was performed to obtain the particle diameter equivalent to the area circle and aspect ratio of each particle. From the result, images of 1,000 particles were arbitrarily extracted from particles in the range of the average of particle diameter equivalent to the area circle ±5 µm and in the range of the average of aspect ratio ±0.1. When the number of the particles in the above ranges is less than 1,000, the image of all particles are used.

The particle shape in the image of each extracted particle was visually confirmed, and a single particle was determined as a primary particle, and aggregated particles were determined as a secondary particle. The ratio of the number of primary particles in 1,000 particles was calculated as a primary particle ratio.

As a simple method, those selecting the range of 1 to X of the luminance dispersion value of the image of each extracted particle are defined as a primary particle, those selecting the range of X to 100 are defined as a secondary particle, and the primary particle ratio (%) can be also calculated by "the number of primary particles/the total number of particles×100". This method experimentally determines X in the range of 1 to 100 so as to match most closely with the primary particle ratio measured by the above visual method, and 30 was adopted as X in the present example.

Herein, the "particle diameter equivalent to the area circle" refers to a method of converting a particle image processed in three dimensions to two dimensions, obtaining a circle having the same circle area as the area thereof, and defining the diameter of the circle as a particle diameter. The "aspect ratio" refers to a ratio obtained by minor axis of particle to major axis of particle.

The "luminance dispersion value" means a standard deviation of luminance of pixels represented at a gray scale level of 0 to 255, and is represented by an equation shown in Mathematical Formula 1. The larger value shows stronger contrast of white and black in the particles, and the smaller value shows particles with lower contrast. Particles overlap each other when forming a secondary particle, thus contrast of particles becomes stronger, and the luminance dispersion value increases.

$$\text{Intensity } SD = \sqrt{\frac{\sum_{i=1}^{N} Ii^2 + \frac{\left(\sum_{i=1}^{N} Ii\right)^2}{N}}{N}}$$ [Mathematical Formula 1]

Ii: Value of intensity of pixel (i)
N; Total number of pixels in particles
<Major Axis to Minor Axis (L/D)>

Images taken by a digital microscope (Type VH-7000 with VH-501 lens, manufactured by KEYENCE Co.) were stored in the form of TIFF file, 1360×1024 pixels, and using an image processing analysis software (Image Hyper II, manufactured by DegiMo Co.), major axis and minor axis of 100 particles were measured to calculate the ratio of L/D, then the average of L/D of 100 particles was obtained.

<Tablet Hardness>

The tablet hardness was measured by a commonly used tablet hardness tester (Tablet Tester 8M/manufactured by DR. SCHLEUNIGER). The tablet hardness of each tablet was measured, and the average of the tablet hardness of 20 tablets was calculated.

<Tablet Disintegration Test>

The test was carried out in accordance with the 16th Revised Japanese Pharmacopoeia, General Tests, Processes and Apparatus "Disintegration Test". Water was used as the test solution.

<Absorbing Capacity of Powder>

According to determination of oil absorption value described in JIS K5101, using pure water in place of oil, 30 ml of pure water was added to 10 g of cellulosic nuclear particles, the mixture was left at room temperature for 1 hour, then the particles were filtered, and water attached to the particle surface was lightly wiped off with a filter paper or the like, then the weight was measured, and the water content was calculated from an increment of the weight and then divided by 10 g.

<Absorbing Capacity of Tablet>

A tablet was placed on a petri dish, the weight of the tablet was measured, and water was slowly added dropwise to the bottom part side of the tablet with a syringe. The weight at the time when the tablet does not absorb water was measured, and absorbing capacity of tablet was calculated by the formula "(tablet weight+weight of absorbed water)/tablet weight×100".

<Tablet Disintegration Test in Oral Cavity>

With three healthy adult male subjects, the time that a tablet was completely disintegrated with saliva in the oral cavity was measured. The time was measured twice for each person, and the average of three person was calculated.

<Ingestion Feel>

With three healthy adult male panelists, ingestion feel of a tablet in the oral cavity was sensuously evaluated. The case where there is no problem in flavor and texture of the tablet was determined as "good", the case where powdery texture was felt was determined as "dry feeling", and the case where roughness of granules or the like was felt was determined as "sense of incongruity". The measurement was performed twice for each person, and only when determined as "good" both times, the evaluation of ingestion feel of the subject was determined as "good". Moreover, for example, in a case where a panelist did not feel anything at the first time, and felt dry feeling at the second time, the evaluation of that panelist was determined as "dry feeling", and in a case where roughness of granules or the like was felt even once, it was determined as "sense of incongruity".

Example 1

Two kilograms of a chopped commercial pulp (polymerization degree: 790) and 30 L of a 4 N hydrochloric acid aqueous solution were placed in a low-speed stirrer (30LGL Reactor, blade diameter: about 30 cm, manufactured by Ikebukuro Horo Kogyo Co., Ltd.), and hydrolyzed at 40° C. for 24 hours while stirring at a stirring rate of 5 rpm to obtain an acid-insoluble residue having an average polymerization degree of 310. The resulting acid-insoluble residue was filtered so as to have a solid content of 40% by mass using a nutsche, and the filtered residue was further washed with purified water and neutralized with aqueous ammonia, then placed in a 90-L plastic bucket, to which purified water was then added, and stirred at a stirring rate of 5 rpm using Three One Motor (Type 1200G, 8M/M, stirring blade diameter: 5 cm, manufactured by HEIDON) to prepare a cellulose dispersion with a solid content concentration of 10% by mass. This was subjected to spray drying (dispersion feed rate: 6 L/hr, inlet temperature: 180 to 220° C., outlet temperature: 50 to 70° C.) and pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder A. The powder physical properties of cellulose powder A are shown in Table 1.

Example 2

A commercial pulp (polymerization degree: 840) was used to carry out the same operation as in Example 1, except that such hydrolysis conditions were a 5 N hydrochloric acid aqueous solution, 40° C. and 60 hours to obtain an acid-insoluble residue with an average polymerization degree of 160. The resulting acid-insoluble residue was not filtered, and washed with pure water and then neutralized, and the material that passed through a sieve with openings of 38 μm was removed without stirring to obtain a cellulose dispersion with a solid content concentration of 10% by mass. The resulting cellulose dispersion was subjected to spray drying using the same operation as in Example 1 and pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder B. The powder physical properties of cellulose powder B are shown in Table 1.

Example 3

A commercial pulp (polymerization degree: 790) was used to carry out the same operation as in Example 1, except that such hydrolysis conditions were a 5 N hydrochloric acid aqueous solution, 40° C., 4 hours and a stirring rate of 30 rpm to obtain an acid-insoluble residue with an average polymerization degree of 440. The resulting acid-insoluble residue was filtered and neutralized using the same operation as in Example 1, followed by stirring at a stirring rate of 500 rpm to obtain a cellulose dispersion with a solid content concentration of 17% by mass. The resulting cellulose dispersion was dried using a drum dryer (Model KDD-1, manufactured Kusunoki Co., Ltd., steam pressure: 0.35 MPa, drum surface temperature: 136° C., drum rotation number: 2 rpm, temperature of a liquid-storing portion: 100° C.), and then pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder C. The powder physical properties of cellulose powder C are shown in Table 1.

Example 4

A commercial microcrystalline cellulose (CEOLUS KG-1000: manufactured by Asahi Kasei Chemicals Corporation) was pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder D. The powder physical properties of cellulose powder D are shown in Table 1.

Example 5

A commercial microcrystalline cellulose (CEOLUS PH-302: manufactured by Asahi Kasei Chemicals Corporation) was pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder E. The powder physical properties of cellulose powder E are shown in Table 1.

Example 6

A commercial microcrystalline cellulose (CEOLUS KG-1000: manufactured by Asahi Kasei Chemicals Corporation) was pulverized at a pulverization pressure of 0.6 MPa and a powder supplying rate of 10 kg/h using a pneumatic pulverizer (Single Track Jet Mill Model STJ-200, manufactured by Seishin Enterprise Co., Ltd.) to obtain cellulose powder F. The powder physical properties of cellulose powder F are shown in Table 1.

Example 7

A commercial microcrystalline cellulose (CEOLUS KG-1000: manufactured by Asahi Kasei Chemicals Corporation) was pulverized at a pulverization pressure of 0.25 MPa and a powder supplying rate of 10 kg/h using a pneumatic pulverizer (Single Track Jet Mill Model STJ-200, manufactured by Seishin Enterprise Co., Ltd.) to obtain cellulose powder G. The powder physical properties of cellulose powder G are shown in Table 1.

Example 8

A commercial microcrystalline cellulose (CEOLUS PH-302: manufactured by Asahi Kasei Chemicals Corporation) was pulverized at a pulverization pressure of 0.8 MPa and a powder supplying rate of 10 kg/h using a pneumatic pulverizer (Single Track Jet Mill Model STJ-200, manufactured by Seishin Enterprise Co., Ltd.) to obtain cellulose powder H. The powder physical properties of cellulose powder H are shown in Table 1.

Example 9

A commercial microcrystalline cellulose (CEOLUS PH-302: manufactured by Asahi Kasei Chemicals Corporation) was pulverized at a pulverization pressure of 0.2 MPa and a powder supplying rate of 10 kg/h using a pneumatic pulverizer (Single Track Jet Mill Model STJ-200, manufactured by Seishin Enterprise Co., Ltd.) to obtain cellulose powder I. The powder physical properties of cellulose powder I are shown in Table 1.

Comparative Example 1

Hydrolysis was carried out by the same operation as in Example 1, except that such hydrolysis conditions were a 3 N hydrochloric acid aqueous solution, 40° C., 20 hours and a stirring rate of 20 rpm to obtain an acid-insoluble residue with an average polymerization degree of 440. The resulting acid-insoluble residue was filtered so as to provide a solid content of 70% by mass using a nutsche. The resulting filtered residue was further washed with purified water and neutralized with aqueous ammonia, then placed in a 90-L plastic bucket, to which purified water was then added, and stirred at a stirring rate of 100 rpm, by the same operation as in Example 1, to prepare a cellulose dispersion with a solid content concentration of 6% by mass. The resulting cellulose dispersion was spray-dried by the same operation as in Example 1 to obtain cellulose powder J. The powder physical properties of cellulose powder J are shown in Table 1.

Comparative Example 2

Hydrolysis was carried out by the same operation as in Example 1, except that such hydrolysis conditions were a 0.14 N hydrochloric acid aqueous solution, 121° C., 1 hour and a stirring rate of 30 rpm to obtain an acid-insoluble residue with an average polymerization degree of 220. The resulting acid-insoluble residue was filtered so as to provide a solid content of 70% by mass using a nutsche. The resulting filtered residue was further washed with purified water and neutralized with aqueous ammonia, then placed in a 90-L plastic bucket, to which purified water was then added, and stirred at a stirring rate of 500 rpm, by the same operation as in Example 1, to prepare a cellulose dispersion with a solid content concentration of 17% by mass. The resulting cellulose dispersion was spray-dried by the same operation as in Example 1, and then coarse particles were removed with a sieve with openings of 325 meshes to obtain cellulose powder K. The powder physical properties of cellulose powder K are shown in Table 1.

Comparative Example 3

A commercial microcrystalline cellulose (CEOLUS PH-101: manufactured by Asahi Kasei Chemicals Corporation) was pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder L. The powder physical properties of cellulose powder L are shown in Table 1.

Comparative Example 4

A commercial microcrystalline cellulose (CEOLUS PH-102: manufactured by Asahi Kasei Chemicals Corporation) was pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder M. The powder physical properties of cellulose powder M are shown in Table 1.

Comparative Example 5

A commercial cellulose powder (trade name: KC FLOCK, manufactured by NIPPON PAPER INDUSTRIES CO., LTD.) was pulverized at a pulverization pressure of 0.4 MPa and a powder supplying rate of 10 kg/h using a pneumatic pulverizer (Single Track Jet Mill Model STJ-200, manufactured by Seishin Enterprise Co., Ltd.) to obtain cellulose powder N. The powder physical properties of cellulose powder N are shown in Table 1.

Comparative Example 6

The same operation as in Example 1 was carried out except for using 2 kg of a chopped commercial pulp (polymerization degree: 1030) to obtain cellulose powder O. The powder physical properties of cellulose powder O are shown in Table 1.

Comparative Example 7

Two kilograms of a chopped commercial pulp (polymerization degree: 790) and 30 L of a 0.14 N hydrochloric acid aqueous solution were placed in a low-speed stirrer (30LGL Reactor, blade diameter: about 30 cm, manufactured by Ikebukuro Horo Kogyo Co., Ltd.), and hydrolyzed at 121° C. for 1 hour while stirring at a stirring rate of 30 rpm to obtain an acid-insoluble residue having an average polymerization degree of 220. The resulting acid-insoluble residue was filtered so as to provide a solid content of 70% by mass using a nutsche, and the filtered residue was further washed with purified water and neutralized with aqueous ammonia, then placed in a 90-L plastic bucket, to which purified water was then added, and stirred at a stirring rate of 500 rpm using Three One Motor (Type 1200G, 8M/M, stirring blade diameter: 5 cm, manufactured by HEIDON) to prepare a cellulose dispersion with a solid content concentration of 17% by mass. This was subjected to spray drying (dispersion feed rate: 6 L/hr, inlet temperature: 180 to 220° C., outlet temperature: 50 to 70° C.) and pulverized at a pulverization pressure of 0.8 MPa and a powder supplying rate of 5 kg/h using a pneumatic pulverizer (Single Track Jet Mill Model STJ-200, manufactured by Seishin Enterprise Co., Ltd.) to obtain cellulose powder P. The powder physical properties of cellulose powder P are shown in Table 1.

Comparative Example 8

A commercial microcrystalline cellulose (CEOLUS KG-1000: manufactured by Asahi Kasei Chemicals Corporation) was pulverized at a pulverization pressure of 0.8 MPa and a powder supplying rate of 5 kg/h using a pneumatic pulverizer (Single Track Jet Mill Model STJ-200, manufactured by Seishin Enterprise Co., Ltd.) to obtain cellulose powder Q. The powder physical properties of cellulose powder Q are shown in Table 1.

Comparative Example 9

A commercial microcrystalline cellulose (CEOLUS KG-1000: manufactured by Asahi Kasei Chemicals Corporation) was pulverized at a pulverization pressure of 0.10 MPa and a powder supplying rate of 20 kg/h using a pneumatic pulverizer (Single Track Jet Mill Model STJ-200, manufactured by Seishin Enterprise Co., Ltd.) to obtain cellulose powder R. The powder physical properties of cellulose powder R are shown in Table 1.

TABLE 1

| | | Cellulose powder | Polymerization degree (—) | Powder physical properties | | | | | |
|---|---|---|---|---|---|---|---|---|---|
| | | | | Average particle diameter (μm) | Apparent bulk density (g/ml) | PEG retention rate (%) | L/D | Primary particle ratio (%) | Absorbing capacity (%) |
| Example | 1 | A | 310 | 30 | 0.14 | 150 | 2.0 | 72 | 360 |
| | 2 | B | 160 | 27 | 0.13 | 138 | 1.7 | 80 | 355 |
| | 3 | C | 440 | 19 | 0.14 | 127 | 2.2 | 69 | 372 |
| | 4 | D | 250 | 25 | 0.13 | 122 | 2.1 | 82 | 386 |
| | 5 | E | 380 | 20 | 0.25 | 135 | 1.7 | 68 | 248 |
| | 6 | F | 250 | 16 | 0.15 | 153 | 1.8 | 80 | 362 |
| | 7 | G | 250 | 33 | 0.12 | 143 | 2.8 | 65 | 350 |
| | 8 | H | 250 | 20 | 0.11 | 153 | 1.5 | 85 | 363 |
| | 9 | I | 250 | 50 | 0.12 | 185 | 3.1 | 53 | 375 |
| Comparative Example | 1 | J | 440 | 38 | 0.21 | 210 | 3.5 | 35 | 375 |
| | 2 | K | 220 | 49 | 0.32 | 135 | 1.3 | 46 | 250 |
| | 3 | L | 310 | 30 | 0.18 | 115 | 1.7 | 38 | 215 |
| | 4 | M | 280 | 26 | 0.16 | 124 | 1.5 | 29 | 227 |
| | 5 | N | 120 | 20 | 0.13 | 107 | 1.2 | 32 | 180 |
| | 6 | O | 310 | 50 | 0.11 | 290 | 3.5 | 30 | 380 |
| | 7 | P | 310 | 4 | 0.12 | 155 | 1.2 | 85 | 365 |

TABLE 1-continued

| | Cellulose powder | Polymerization degree (—) | Average particle diameter (µm) | Apparent bulk density (g/ml) | PEG retention rate (%) | L/D | Primary particle ratio (%) | Absorbing capacity (%) |
|---|---|---|---|---|---|---|---|---|
| 8 | Q | 280 | 5 | 0.11 | 150 | 1.2 | 65 | 370 |
| 9 | R | 280 | 50 | 0.12 | 285 | 1.4 | 40 | 375 |

Example 10

In a mortar (using the material SUK 2, 3, manufactured by Kikusui Seisakusho Ltd.) was placed 0.5 g of each of the resulting cellulose powders obtained in Examples 1 to 9, and compressed at a tableting compression force of 2.0 kN with a round plane pestle with 1.13 cm in diameter (using the material SUK 2, 3, manufactured by Kikusui Seisakusho Ltd.). The compression force was maintained for 10 seconds to prepare a tablet (PCM-1A manufactured by Aikoh Engineering Co., Ltd. was used as a compressor). The hardness of the resulting tablet is shown in Table 2.

Comparative Example 10

In a mortar (using the material SUK 2, 3, manufactured by Kikusui Seisakusho Ltd.) was placed 0.5 g of each of the resulting cellulose powders obtained in Comparative Examples 1 to 9, and compressed at a tableting compression force of 2 kN with a round plane pestle with 1.13 cm in diameter (using the material SUK 2, 3, manufactured by Kikusui Seisakusho Ltd.). The compression force was maintained for 10 seconds to prepare a tablet (PCM-1A manufactured by Aikoh Engineering Co., Ltd. was used as a compressor). The hardness of the resulting tablet is shown in Table 2.

TABLE 2

Tableting compression force: 2 kN
500 mg Tablet, 11.3 mmϕ, Flat tablet

| | | Cellulose powder | Tablet hardness (N) |
|---|---|---|---|
| Example | 1 | A | 267 |
| | 2 | B | 255 |
| | 3 | C | 240 |
| | 4 | D | 280 |
| | 5 | E | 235 |
| | 6 | F | 275 |
| | 7 | G | 260 |
| | 8 | H | 300 |
| | 9 | I | 260 |
| Comparative Example | 1 | J | 250 |
| | 2 | K | 180 |
| | 3 | L | 175 |
| | 4 | M | 168 |
| | 5 | N | 130 |
| | 6 | O | 265 |
| | 7 | P | 288 |
| | 8 | Q | 185 |
| | 9 | R | 170 |

Example 11

In a mortar (using the material SUK 2, 3, manufactured by Kikusui Seisakusho Ltd.) was placed 0.5 g of each of the resulting cellulose powders obtained in Examples 1 to 9, in the same manner as in Example 10, and compressed at a tableting compression force lower than that in Example 10 with a round plane pestle with 1.13 cm in diameter (using the material SUK 2, 3, manufactured by Kikusui Seisakusho Ltd.) to prepare a tablet with a tablet hardness of around 60 N. The absorbing capacity of the resulting tablet is shown in Table 3.

Comparative Example 11

In a mortar (using the material SUK 2, 3, manufactured by Kikusui Seisakusho Ltd.) was placed 0.5 g of each of the resulting cellulose powders obtained in Comparative Examples 1 to 9, in the same manner as in Comparative Example 10, and compressed at a tableting compression force lower than that in Comparative Example 6 with a round plane pestle with 1.13 cm in diameter (using the material SUK 2, 3, manufactured by Kikusui Seisakusho Ltd.) to prepare a tablet with a tablet hardness of around 60 N. The absorbing capacity of the resulting tablet is shown in Table 3.

TABLE 3

Tablet hardness: 60 kN
500 mg Tablet, 11.3 mmϕ, Flat tablet

| | | Cellulose powder | Absorbing capacity (%) |
|---|---|---|---|
| Example | 1 | A | 145 |
| | 2 | B | 137 |
| | 3 | C | 148 |
| | 4 | D | 150 |
| | 5 | E | 111 |
| | 6 | F | 160 |
| | 7 | G | 165 |
| | 8 | H | 140 |
| | 9 | I | 190 |
| Comparative Example | 1 | J | 186 |
| | 2 | K | 210 |
| | 3 | L | 155 |
| | 4 | M | 135 |
| | 5 | N | 144 |
| | 6 | O | 186 |
| | 7 | P | 146 |
| | 8 | Q | 160 |
| | 9 | R | 140 |

Example 12

In a tumbler mixer (TM-50S type; Dalton) were charged 1.12 kg of erythritol (Cargill Japan), 0.48 kg of each of the cellulose powders obtained in Examples 1 to 9 and 1.60 kg of N-acetyl glucosamine (Yaizu Suisankagaku Industry Co., Ltd.), and the mixture was mixed for 20 minutes. Then, the mixture was taken out, introduced into a high-speed agitation granulator (vertical granulator VG-10; POWREX), and granulated. Granulation conditions were as follows.

(1) Broad rotation speed: 500 rpm
(2) Chopper rotation speed: 1500 rpm
(3) Granulation time: 3 minutes
(4) Added water amount: 0.24 kg The granulated granules were taken out and charged in a fluidized bed type dryer to be dried. Drying conditions were as follows.
(A) Used device: MULTIPLEX (trade name), MP-01 type, Powrex Corporation
(B) Air volume: 7 m³/min
(C) Air supply temperature: 70 to 75° C.
(D) Exhaust temperature at stoppage: 45° C.

The dried granules were taken out, and sized by a sieve mesh of 710 μm, then the particle size distribution of the granules was measured to obtain an average particle diameter. The average particle diameter of the granules is shown in Table 4.

TABLE 4

|  | Granule diameter [μm] |
|---|---|
| Example 1 | 321.5 |
| Example 2 | 313.5 |
| Example 3 | 302.0 |
| Example 4 | 293.5 |
| Example 5 | 297.0 |
| Example 6 | 305.2 |
| Example 7 | 321.3 |
| Example 8 | 310.7 |
| Example 9 | 322.9 |

36 g of pregelatinized starch (trade name SWELSTAR FD-1: Asahi Kasei Chemicals Corporation) and 14 g of ascorbic acid (Takeda Pharmaceutical Company Limited.) were added to 1200 g of the granules, and the mixture was charged in a tumbler mixer (TM-50S type; Dalton) and mixed for 20 minutes. Thereafter, 12 g of calcium stearate (TAIHEI CHEMICAL INDUSTRIAL CO., LTD.) was added thereto, and the mixture was mixed for further 3 minutes, and taken out. The weight ratio of the cellulose powder of the mixed powder was 28.5%, and the mixed powder was charged in a tableting machine (Libra 2 (trade name); Kikusui Seisakusho Ltd.) to prepare a tablet. Tableting conditions were as follows. The mixed powder was able to be all tableted without tableting troubles, and the ingestion feel of the tablet in the oral cavity was a satisfactory result as an orally disintegrating tablet without feeling roughness and dryness. Physical properties and evaluation results of the resulting tablet are shown in Table 5.
(A) Tablet weight: 280 mg
(B) Tablet diameter: 8 mmφ, 12 R
(C) Rotor rotational speed: 45 rpm
(D) Feeder type: Open feeder
(E) Tableting compression force: 5 kN
(F) Tableting time: 10 minutes
(g) Number of mortar and pestle: 12

TABLE 5

| | Cellulose powder | Tablet hardness [N] 50N or more | Tablet disintegration test [sec] 30 seconds or less | Tablet oral test [sec] 30 seconds or less | Ingestion feel Good Dry feeling Sense of incongruity |
|---|---|---|---|---|---|
| Example 1 | A | 65 | 28 | 26 | Good |
| Example 2 | B | 63 | 25 | 25 | Good |
| Example 3 | C | 60 | 22 | 21 | Good |
| Example 4 | D | 72 | 26 | 25 | Good |
| Example 5 | E | 58 | 23 | 24 | Good |
| Example 6 | F | 70 | 26 | 25 | Good |
| Example 7 | G | 65 | 25 | 23 | Good |
| Example 8 | H | 90 | 25 | 23 | Good |
| Example 9 | I | 65 | 26 | 25 | Good |

Example 13

0.42 kg of erythritol (Cargill Japan), 0.18 kg of each of the cellulose powders obtained in Examples 1 to 9 and 0.60 kg of N-acetyl glucosamine (Yaizu Suisankagaku Industry Co., Ltd.), 36 g of SWELSTAR FD-1 (trade name) (Asahi Kasei Chemicals Corporation) and 14 g of ascorbic acid (Takeda Pharmaceutical Company Limited.) were added, and the mixture was charged in a tumbler mixer (TM-50S type; Dalton) and mixed for 20 minutes. Thereafter, 12 g of calcium stearate (TAIHEI CHEMICAL INDUSTRIAL CO., LTD.) was added thereto, and the mixture was mixed for further 3 minutes, and taken out. The weight ratio of the cellulose powder of the mixed powder was 14.3%, and the mixed powder was charged in a tableting machine (Libra 2 (trade name); Kikusui Seisakusho Ltd.) to prepare a tablet. Tableting conditions were as follows. The mixed powder was able to be all tableted without tableting troubles, and the ingestion feel of the tablet in the oral cavity was a satisfactory result as an orally disintegrating tablet without feeling roughness and dryness. Physical properties and evaluation results of the resulting tablet are shown in Table 6.
(A) Tablet weight: 280 mg
(B) Tablet diameter: 8 mmφ, 12 R
(C) Rotor rotational speed: 45 rpm
(D) Feeder type: Open feeder
(E) Tableting compression force: 5 kN
(F) Tableting time: 10 minutes
(g) Number of mortar and pestle: 12

TABLE 6

| | Cellulose powder | Tablet hardness [N] 50N or more | Tablet disintegration test [sec] 30 seconds or less | Tablet oral test [sec] 30 seconds or less | Ingestion feel Good Dry feeling Sense of incongruity |
|---|---|---|---|---|---|
| Example 1 | A | 63 | 27 | 25 | Good |
| Example 2 | B | 60 | 26 | 25 | Good |
| Example 3 | C | 57 | 23 | 24 | Good |
| Example 4 | D | 68 | 25 | 23 | Good |
| Example 5 | E | 55 | 21 | 20 | Good |
| Example 6 | F | 65 | 25 | 23 | Good |
| Example 7 | G | 62 | 24 | 22 | Good |
| Example 8 | H | 80 | 25 | 23 | Good |
| Example 9 | I | 55 | 24 | 22 | Good |

Comparative Example 12

In a tumbler mixer (TM-50S type; Dalton) were charged 1.12 kg of erythritol (Cargill Japan), 0.48 kg of each of the cellulose powders obtained in Comparative Examples 1 to 9 and 1.60 kg of N-acetyl glucosamine (Yaizu Suisankagaku Industry Co., Ltd.), and mixed for 20 minutes. Then, the mixture was taken out, introduced into a high-speed agitation granulator (vertical granulator VG-10; POWREX), and granulated. Granulation conditions were as follows.
(1) Broad rotation speed: 500 rpm
(2) Chopper rotation speed: 1500 rpm
(3) Granulation time: 3 minutes
(4) Added water amount: 0.24 kg The granulated granules were taken out and charged in a fluidized bed type dryer to be dried. Drying conditions were as follows.
(A) Used device: MULTIPLEX (trade name), MP-01 type, Powrex Corporation
(B) Air volume: 7 m³/min
(C) Air supply temperature: 70 to 75° C.
(D) Exhaust temperature at stoppage: 45° C.

The dried granules were taken out, and sized by a sieve mesh of 710 μm, then the particle size distribution of the granules was measured to obtain an average particle diameter. The average particle diameter of the granules is shown in Table 7.

TABLE 7

| | Granule diameter [μm] |
|---|---|
| Comparative Example 1 | 295.0 |
| Comparative Example 2 | 313.0 |
| Comparative Example 3 | 306.5 |
| Comparative Example 4 | 305.5 |
| Comparative Example 5 | 307.5 |
| Comparative Example 6 | 310.5 |

TABLE 7-continued

| | Granule diameter [μm] |
|---|---|
| Comparative Example 7 | 326.7 |
| Comparative Example 8 | 318.4 |
| Comparative Example 9 | 317.1 |

36 g of SWELSTAR FD-1 (trade name) (Asahi Kasei Chemicals Corporation) and 14 g of ascorbic acid (Takeda Pharmaceutical Company Limited.) were added to 1200 g of the granules, and the mixture was charged in a tumbler mixer (TM-50S type; Dalton) and mixed for 20 minutes. Thereafter, 12 g of calcium stearate (TAIHEI CHEMICAL INDUSTRIAL CO., LTD.) was added thereto, and the mixture was mixed for further 3 minutes, and taken out. The weight ratio of the cellulose powder of the mixed powder was 28.5%, and the mixed powder was charged in a tableting machine (Libra 2 (trade name); Kikusui Seisakusho Ltd.) to prepare a tablet. Tableting conditions were as follows. While the mixed powder was able to be all tableted without tableting troubles, the ingestion feel of the tablet in the oral cavity was not a satisfactory result as an orally disintegrating tablet with feeling roughness and dryness. Physical properties and evaluation results of the resulting tablet are shown in Table 8.
(A) Tablet weight: 280 mg
(B) Tablet diameter: 8 mmφ, 12 R
(C) Rotor rotational speed: 45 rpm
(D) Feeder type: Open feeder
(E) Tableting compression force: 5 kN
(F) Tableting time: 10 minutes
(g) Number of mortar and pestle: 12

TABLE 8

| | Cellulose powder | Tablet hardness [N] 50N or more | Tablet disintegration test [sec] 30 seconds or less | Tablet oral test [sec] 30 seconds or less | Ingestion feel Good Dry feeling Sense of incongruity | Remark |
|---|---|---|---|---|---|---|
| Comparative Example 1 | J | 60 | 26 | 28 | Dry feeling Sense of incongruity | — |
| Comparative Example 2 | K | 53 | 20 | 24 | Dry feeling Sense of incongruity | — |
| Comparative Example 3 | L | 50 | 20 | 22 | Dry feeling | — |
| Comparative Example 4 | M | 45 | 18 | 20 | Dry feeling | Insufficient moldability |
| Comparative Example 5 | N | 38 | 15 | 16 | Dry feeling | Insufficient moldability |
| Comparative Example 6 | O | 63 | 28 | 27 | Dry feeling | — |
| Comparative Example 7 | P | 68 | 24 | 21 | Sense of incongruity (hard) | Flowability deterioration |
| Comparative Example 8 | Q | 50 | 20 | 21 | Sense of incongruity (hard) | Flowability deterioration |
| Comparative Example 9 | R | 47 | 19 | 20 | Dry feeling | — |

At a hardness of 50N or less, moldability of a tablet is insufficient, and the tablet chips and cracks during transportation and storage, thus a quality problem is caused.

Comparative Example 13

0.42 kg of erythritol (Cargill Japan), 0.18 kg of each of the cellulose powders obtained in Comparative Examples 1 to 9 and 0.60 kg of N-acetyl glucosamine (Yaizu Suisankagaku Industry Co., Ltd.), 36 g of SWELSTAR FD-1 (trade name) (Asahi Kasei Chemicals Corporation) and 14 g of ascorbic acid (Takeda Pharmaceutical Company Limited.) were added, and the mixture was charged in a tumbler mixer (TM-50S type; Dalton) and mixed for 20 minutes. Thereafter, 12 g of calcium stearate (TAIHEI CHEMICAL INDUSTRIAL CO., LTD.) was added thereto, and the mixture was mixed for further 3 minutes, and taken out. The weight ratio of the cellulose powder of the mixed powder was 14.3%, and the mixed powder was charged in a tabletting machine (Libra 2 (trade name); Kikusui Seisakusho Ltd.) to prepare a tablet. Tabletting conditions were as follows. While the mixed powder was able to be all tabletted without tabletting troubles, the ingestion feel of the tablet in the oral cavity was not a satisfactory result as an orally disintegrating tablet with feeling roughness and dryness. Physical properties and evaluation results of the resulting tablet are shown in Table 9.

(A) Tablet weight: 280 mg
(B) Tablet diameter: 8 mmϕ, 12 R
(C) Rotor rotational speed: 45 rpm
(D) Feeder type: Open feeder
(E) Tabletting compression force: 5 kN
(F) Tabletting time: 10 minutes
(g) Number of mortar and pestle: 12

TABLE 9

| | Cellulose powder | Tablet hardness [N] 50N or more | Tablet disintegration test [sec] 30 seconds or less | Tablet oral test [sec] 30 seconds or less | Ingestion feel Good Dry feeling Sense of incongruity | Remark |
|---|---|---|---|---|---|---|
| Comparative Example 1 | J | 53 | 23 | 23 | Dry feeling Sense of incongruity | — |
| Comparative Example 2 | K | 42 | 18 | 21 | Dry feeling Sense of incongruity | Insufficient moldability |
| Comparative Example 3 | L | 40 | 18 | 20 | Dry feeling | Insufficient moldability |
| Comparative Example 4 | M | 38 | 13 | 16 | Dry feeling | Insufficient moldability |
| Comparative Example 5 | N | 32 | 12 | 13 | Dry feeling | Insufficient molability |
| Comparative Example 6 | O | 55 | 24 | 23 | Dry feeling | — |
| Comparative Example 7 | P | 59 | 26 | 25 | Sense of incongruity (hard) | Flowability deterioration |
| Comparative Example 8 | Q | 45 | 20 | 21 | Sense of incongruity (hard) | Flowability deterioration |
| Comparative Example 9 | R | 40 | 19 | 19 | Dry feeling | — |

Reference Example 0.62 kg of erythritol (Cargill Japan), 0.18 kg of each of the cellulose powders obtained in Examples 1 to 9 and 0.40 kg of curcumin powder, 36 g of SWELSTAR FD-1 (trade name) (Asahi Kasei Chemicals Corporation) and 14 g of ascorbic acid (Takeda Pharmaceutical Company Limited.) were added, and the mixture was charged in a tumbler mixer (TM-50S type; Dalton) and mixed for 20 minutes. Thereafter, 12 g of calcium stearate (TAIHEI CHEMICAL INDUSTRIAL CO., LTD.) was added thereto, and the mixture was mixed for further 3 minutes, and taken out. The weight ratio of the cellulose powder of the mixed powder was 14.3%, and the mixed powder was charged in a tabletting machine (Libra 2 (trade name); Kikusui Seisakusho Ltd.) to prepare a tablet. Tabletting conditions were as follows. While the mixed powder was able to be all tabletted without tabletting troubles, the ingestion feel of the cellulose powders of Examples 8 and 9 in the oral cavity was not a satisfactory result as an orally disintegrating tablet with feeling roughness and dryness. Physical properties and evaluation results of the resulting tablet are shown in Table 10.

(A) Tablet weight: 280 mg
(B) Tablet diameter: 8 mmϕ, 12 R
(C) Rotor rotational speed: 45 rpm
(D) Feeder type: Open feeder
(E) Tabletting compression force: 5 kN
(F) Tabletting time: 10 minutes
(g) Number of mortar and pestle: 12

TABLE 10

| | Cellulose powder | Tablet hardness [N] 50N or more | Tablet disintegration test [sec] 30 seconds or less | Tablet oral test [sec] 30 seconds or less | Ingestion feel Good Dry feeling Sense of incongruity |
|---|---|---|---|---|---|
| Example 1 | A | 72 | 28 | 26 | Good |
| Example 2 | B | 70 | 27 | 24 | Good |
| Example 3 | C | 67 | 25 | 25 | Good |
| Example 4 | D | 79 | 28 | 27 | Good |
| Example 5 | E | 66 | 24 | 24 | Good |
| Example 6 | F | 77 | 27 | 28 | Good |
| Example 7 | G | 73 | 28 | 25 | Good |
| Example 8 | H | 90 | 27 | 26 | Dry feeling Sense of incongruity |

TABLE 10-continued

| Cellulose powder | Tablet hardness [N] 50N or more | Tablet disintegration test [sec] 30 seconds or less | Tablet oral test [sec] 30 seconds or less | Ingestion feel Good Dry feeling Sense of incongruity |
|---|---|---|---|---|
| Example 9 I | 66 | 28 | 24 | Dry feeling Sense of incongruity |

INDUSTRIAL APPLICABILITY

The present invention can be suitably used in the fields of pharmaceutical formulation containing a pharmaceutical drug, health food, and food. The present invention has particularly excellent disintegration properties, and thus can be used as a disintegrating solid formulation that can be taken without water, preferably as a solid formulation (tablet) that is rapidly disintegrable in the oral cavity.

The invention claimed is:

1. A cellulose powder with an average polymerization degree of 150 to 450, an average particle diameter of not less than 10 μm but less than 100 μm, and a primary particle ratio of 50% or more and wherein particles of the cellulose powder have a ratio of major axis to minor axis (L/D) of 1.8 to 2.8.

2. The cellulose powder according to claim 1, wherein a retention rate of polyethylene glycol with an average molecular weight of 400 is less than 190%, a tablet absorbing capacity at a tablet hardness of 60 N is 170% or less, and a tablet hardness at a tableting compression force of 2.0 kN is 130 N or more.

3. An orally disintegrating tablet comprising the cellulose powder of claim 1.

4. A method for producing an orally disintegrating tablet comprising:
   admixing 3 to 99% by mass of a cellulose powder as claimed in claim 1, and 1 to 97% by mass of a component comprising: a drug or an active ingredient of a drug to obtain a mixture, and
   compression molding the mixture.

5. The cellulose powder according to claim 1, wherein a retention rate of polyethylene glycol with an average molecular weight of 400 is less than 180%, a tablet absorbing capacity at a tablet hardness of 60 N is not less than 50% but not more than 170%, and a tablet hardness at a tableting compression force of 2.0 kN is 150 N or more.

6. An orally disintegrating tablet comprising the cellulose powder of claim 2.

7. An orally disintegrating tablet comprising the cellulose powder of claim 5.

8. A method for producing an orally disintegrating tablet comprising:
   admixing 3 to 99% by mass of a cellulose powder as claimed in claim 2, and 1 to 97% by mass of a component comprising: a drug or an active ingredient of a drug to obtain a mixture, and
   compression molding the mixture.

9. A method for producing an orally disintegrating tablet comprising:
   admixing 3 to 99% by mass of a cellulose powder as claimed in claim 5, and 1 to 97% by mass of a component comprising: a drug or an active ingredient of a drug to obtain a mixture and
   compression molding the mixture.

10. The method for producing an orally disintegrating tablet according to claim 4, wherein the component further comprises: an excipient, a binder, a disintegrant, or a lubricant.

11. The method for producing an orally disintegrating tablet according to claim 8, wherein the component further comprises: an excipient, a binder, a disintegrant, or a lubricant.

12. The method for producing an orally disintegrating tablet according to claim 9, wherein the component further comprises: an excipient, a binder, a disintegrant, or a lubricant.

* * * * *